(12) United States Patent
Kalbassi et al.

(10) Patent No.: US 9,108,145 B2
(45) Date of Patent: Aug. 18, 2015

(54) PURIFICATION OF AIR

(71) Applicant: AIR PRODUCTS AND CHEMICALS INC., Allentown, PA (US)

(72) Inventors: Mohammad Ali Kalbassi, Weybridge (GB); Anthony Finot, London (GB); Timothy Christopher Golden, Brittany (FR); Christopher James Raiswell, Crewe (GB); Ann Marie Botelho, Centre Valley, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 341 days.

(21) Appl. No.: 13/895,632

(22) Filed: May 16, 2013

(65) Prior Publication Data

US 2014/0338425 A1    Nov. 20, 2014

(51) Int. Cl.
*B01D 53/04*     (2006.01)
*F25J 3/04*      (2006.01)
(Continued)

(52) U.S. Cl.
CPC .......... *B01D 53/0462* (2013.01); *B01D 53/047* (2013.01); *F25J 3/04169* (2013.01);
(Continued)

(58) Field of Classification Search
CPC ............. B01D 53/0462; B01D 53/047; B01D 2253/104; B01D 2253/108; B01D 2257/402; B01D 2257/504; B01D 2257/80; B01D 2259/40013; B01D 2259/4002; B01D 2259/40028; B01D 2259/40043; B01D 2259/40056; B01D 2259/4145; F25J 3/04169; F25J 3/04775; F25J 3/04854; F25J 2205/60; F25J 2205/70; G01N 33/0036; G01N 33/004; Y02C 10/08; Y02C 20/10; Y10T 29/4973
USPC ........ 95/8, 11, 96, 99, 106, 129, 139; 96/111, 96/132
See application file for complete search history.

(56) References Cited

U.S. PATENT DOCUMENTS

| 4,249,915 A | 2/1981 | Sircar et al. |
| 4,472,178 A | 9/1984 | Kumar et al. |

(Continued)

FOREIGN PATENT DOCUMENTS

| CA | 804391 A | 1/1969 |
| EP | 0992274 A1 | 4/2000 |

(Continued)

OTHER PUBLICATIONS

U. Gemmingen, "Designs of adsorptive dryers in air separation plants," Reports on Science and Technology, Linde, 54, 1994, pp. 8-12.

(Continued)

*Primary Examiner* — Frank Lawrence
(74) *Attorney, Agent, or Firm* — Eric J. Schaal

(57) ABSTRACT

Process of reducing water, $CO_2$ and $N_2O$ in feed air, which: a first adsorbent such as alumina (25-40% volume) and a second adsorbent such as X zeolite (60-75% volume) are used; the online time of the adsorbent is determined by determining the concentration measured by an analyzer for $CO_2$ concentration at a position within the length of the second adsorbent when a maximum level of $N_2O$ is simultaneously obtained at the downstream end of the second adsorbent in the feed direction, wherein the online time is the time taken from commencing passing the feed air to the first and second adsorbents to the measurement by the analyzer of the determined concentration of $CO_2$; at least the second adsorbent is regenerated by heated regeneration gas at a temperature of 140° C.-220° C.; and the molar ratio of the regenerating gas to feed air supplied during one iteration of the cycle is 0.08-0.5.

27 Claims, 5 Drawing Sheets

(51) Int. Cl.
  *B01D 53/047* (2006.01)
  *G01N 33/00* (2006.01)

(52) U.S. Cl.
  CPC .......... *F25J3/04775* (2013.01); *F25J 3/04854* (2013.01); *G01N 33/004* (2013.01); *G01N 33/0036* (2013.01); *B01D 2253/104* (2013.01); *B01D 2253/108* (2013.01); *B01D 2257/402* (2013.01); *B01D 2257/504* (2013.01); *B01D 2257/80* (2013.01); *B01D 2259/4002* (2013.01); *B01D 2259/40013* (2013.01); *B01D 2259/40028* (2013.01); *B01D 2259/40043* (2013.01); *B01D 2259/40056* (2013.01); *B01D 2259/4145* (2013.01); *F25J 2205/60* (2013.01); *F25J 2205/70* (2013.01); *Y02C 10/08* (2013.01); *Y02C 20/10* (2013.01); *Y10T 29/4973* (2015.01)

(56) References Cited

U.S. PATENT DOCUMENTS

| | | |
|---|---|---|
| 4,541,851 A | 9/1985 | Bosquain et al. |
| 4,711,645 A | 12/1987 | Kumar |
| 5,137,548 A | 8/1992 | Grenier et al. |
| 5,232,474 A | 8/1993 | Jain |
| 5,614,000 A | 3/1997 | Kalbassi et al. |
| 5,656,064 A | 8/1997 | Golden et al. |
| 5,846,295 A | 12/1998 | Kalbassi et al. |
| 5,855,650 A | 1/1999 | Kalbassi et al. |
| 5,980,611 A | 11/1999 | Kumar et al. |
| 6,106,593 A | 8/2000 | Golden et al. |
| 6,599,347 B2 | 7/2003 | Kalbassi et al. |
| 6,719,827 B2 | 4/2004 | Golden et al. |
| 7,413,595 B2 | 8/2008 | Schmidt et al. |
| 7,524,358 B2 * | 4/2009 | Saxena et al. .................. 95/118 |
| 7,759,288 B2 | 7/2010 | Prichett et al. |
| 7,935,177 B2 | 5/2011 | Lutz et al. |
| 8,734,571 B2 * | 5/2014 | Golden et al. .................. 95/97 |
| 2006/0162556 A1 | 7/2006 | Ackley et al. |

FOREIGN PATENT DOCUMENTS

| | | |
|---|---|---|
| EP | 1245266 A2 | 10/2002 |
| EP | 1961477 A1 | 8/2008 |
| JP | 11316082 | 3/1999 |
| JP | 2000279740 A | 10/2000 |
| JP | 2004148315 | 5/2004 |
| JP | 2004000975 A | 8/2004 |
| JP | 2004232967 | 8/2004 |
| JP | 2005013832 A | 1/2005 |
| JP | 2011153183 A | 8/2011 |
| WO | 2005000447 A1 | 1/2005 |
| WO | 2007069605 A1 | 6/2007 |
| WO | PCT/EP2012/060317 | 5/2012 |

OTHER PUBLICATIONS

C.W. Skarstrom, "Heatless Fractionation of Gases Over Solid Adsorbents," vol. II, 95, N. W. Li (Ed), CRC Press, Cleveland, Ohio 1972, pp. 95-106.

U. Wenning, "Nitroux Oxides in Air Separation Plants," Proceedings from MUST '96, pp. 32-36, (1996).

* cited by examiner

PURIFICATION OF AIR

BACKGROUND

The invention relates to the removal of water, carbon dioxide and nitrous oxide, and optionally also hydrocarbons, from an air stream prior to cryogenic air separation.

The cryogenic separation of air requires a pre-purification step for the removal of both high-boiling and hazardous materials. Principal high-boiling air components include water and carbon dioxide. If removal of these impurities from ambient feed air is not achieved, then water and carbon dioxide may freeze out in cold sections of the separation process, such as heat exchangers and the liquid oxygen (LOX) sump. This may cause pressure drop, flow variations and operational problems. Various hazardous materials have also to be recovered including acetylene and other hydrocarbons. The high boiling hydrocarbons, if not removed, may concentrate in the LOX section of the column, resulting in a potential explosive hazard.

It is known that oxides of nitrogen should be removed also. A minor air component is nitrous oxide $N_2O$, which is present in ambient air at about 0.3 ppm. It has similar physical properties to carbon dioxide and therefore presents a potential operation problem because of solids formation in the column and heat exchangers of the cryogenic distillation apparatus. In addition, nitrous oxide is known to enhance combustion of organic materials and is shock sensitive. As such, nitrous oxide also presents a safety hazard. Hydrocarbons such as ethylene, acetylene, butane, propylene and propane are further impurities which are desirably removed prior to cryogenic air separation.

The pre-purification of air is usually conducted by adsorptive clean up processes. These may operate by thermal swing adsorption (TSA) as described in U.S. Pat. No. 4,541,851 and 5,137,548 or U. Gemmingen ("Designs of Adsorptive Driers in Air Separation Plants" Reports on Technology 54/1994, Linde), by pressure swing adsorption (PSA) as described in U.S. Pat. No. 4,711,645, U.S. Pat. No. 5,232,474 or C. W. Skarstrom ("Heatless Fractionation of Gases over Solid Adsorbents" vol II, 95, N. W. Li (Ed), CRC Press, Cleveland, Ohio 1972), or by variants of those processes such as thermally enhanced PSA (TEPSA) as described in U.S. Pat. No. 5,614,000 or TPSA as described in U.S. Pat. No. 5,855,650.

In general, pre-purification of air is carried out by adsorption of contaminating gas components from the air by adsorption on a solid adsorbent with periodic regeneration of the adsorbent. In such methods, the air is fed in contact with at least two layers of solid adsorbents to adsorb the components to be removed, the concentration of which components gradually increases in the adsorbents. The concentration of each of the removed gas components in the adsorbent will not be uniform but will be highest at the upstream end of the adsorbent bed and will tail off progressively through a mass transfer zone in the adsorbent. If the process is conducted indefinitely, the mass transfer zone will progressively move downstream in the adsorbent bed until the component which is to be removed breaks through from the downstream end of the bed. Before this occurs, it is necessary to regenerate the adsorbent.

In pressure swing adsorption (PSA) systems, this is done by stopping the flow into the adsorbent of the gas to be treated, depressurising the adsorbent and, usually, by passing a flow of a regenerating gas low in its content of the component adsorbed on the bed through the bed counter-current to the product feed direction. As the component which is being removed is adsorbed while the bed is on-line, the adsorption process will generate heat of adsorption causing a heat pulse to progress downstream through the adsorbent. During the regeneration process, heat must be supplied to desorb the gas component which has been adsorbed on the bed. In PSA, one aims to commence regeneration before the heat pulse has reached the downstream end of the bed; the direction of travel of the heat pulse is reversed by the counter-current flow of the regenerating gas and the heat derived from the adsorption of the gas component in question is used for desorbing that component during regeneration. One thus avoids having to supply heat during the regeneration step. However, the short cycle time (feed time of typically 10-15 min) used in order to avoid the heat pulse leaving the adsorbent bed requires frequent depressurisation of the bed, during which the feed gas is vented off and lost ("switch loss"). In addition, it is usual to use two adsorbent beds, with one being on-line while the other is regenerated. The depressurisation and regeneration of one bed must take place during the short time for which the other bed is on-line, and rapid repressurisation can lead to transient variations in the feed and product flows which can adversely affect plant operation.

An alternative procedure is known as temperature swing adsorption (TSA). In TSA, the cycle time is extended (feed time of typically 2-12 h) and the heat pulse mentioned above is allowed to proceed out of the downstream end of the adsorbent bed during the feed or on-line period. To achieve regeneration, it is therefore necessary to supply heat to desorb the adsorbed gas component. To this end, the regenerating gas used is heated for a period to produce a heat pulse moving through the bed counter-current to the normal feed direction. This flow of heated regenerating gas is usually followed by a flow of cool regenerating gas which continues the displacement of the heat pulse through the bed towards the upstream end. TSA is characterised by an extended cycle time as compared to PSA. TSA is energy intensive because it is necessary to supply regenerating gas heated to a high temperature such as 150-200 C in order to ensure desorption of the more strongly adsorbed component from the bed. It is usual also to pre-cool the air to be treated in order to minimise the amount of water that must be adsorbed on the bed, further increasing plant and energy costs.

In a typical air pre-purification TSA method, a two-layer bed is employed to remove essentially all of the water and carbon dioxide present in the feed air stream. Since water is the more strongly adsorbed of the two species, the beds are usually run until carbon dioxide starts to break through the adsorbent bed. More $CO_2$ than $N_2O$ is present in the feed air stream, but since 13X has a larger capacity for $CO_2$ than for $N_2O$, if the beds are run to $CO_2$ breakthrough, significant amounts of $N_2O$ will break through from the bed, and may cause problems downstream in the cryogenic distillation plant.

U.S. Pat. No. 4,249,915 and U.S. Pat. No. 4,472,178 disclose an adsorption process in which moisture and carbon dioxide are removed from atmospheric air by adsorption in separate respective beds. The moisture laden bed is regenerated by PSA in a relatively short operating cycle, while the carbon dioxide laden bed is regenerated thermally at considerably longer time intervals. While there are certain benefits to this arrangement, the plant costs are high due to duplication of columns and the need for additional equipment to carry out both systems of regeneration of the respective beds.

Wenning ("Nitrous oxides in Air Separation Plants" U. Wenning, Proceedings from MUST 96, pp 79-89) describes how carbon dioxide can displace already adsorbed nitrous oxide from a zeolite adsorbent, causing breakthrough of nitrous oxide at a concentration greater than that in ambient air.

U.S. Pat. No. 5,919,286 teaches that a layer of zeolite (17% by volume) at the product (downstream) end of an alumina bed can be used for nitrogen oxides removal in a PSA process.

EP0992274 describes a process for the removal of carbon dioxide, water and nitrous oxide from air preferably in a TSA process, in which a three-layer adsorbent bed is used, with a first layer, for example of alumina, primarily adsorbing water, a second layer, for example of 13X, primarily adsorbing carbon dioxide, and a third layer, for example of CaX, primarily adsorbing nitrous oxide.

U.S. Pat. No. 5,846,295 describes a TSA process for the removal of $CO_2$ and $H_2O$ in which impregnated alumina is used, in some cases in combination with a zeolite such as 13X at the product end of the bed. The process is run to $CO_2$ breakthrough from the end of the bed, and the ratio of heating time to online time required to desorb the $CO_2$ and water adsorbed on the bed is between 54% and 38%.

U.S. Pat. No. 5,614,000 describes a process for removal of water and $CO_2$ from air in which an adsorbent bed, preferably containing only alumina, may be regenerated partially by TSA and partially by PSA, with the part of the adsorbent that adsorbs water (the upstream part) being regenerated by PSA whereas the remainder is regenerated by TSA using a regenerating gas temperature of around 70° C. Such a process is known by the acronym TEPSA. This process is run to $CO_2$ breakthrough from the end of the bed, and the ratio of heating time to online time required to desorb the $CO_2$ and water adsorbed on the bed is typically about 33% (Tables 2 and 3 show heat time/on-line time of 10/30=0.33).

U.S. Pat. No. 5,855,650 describes a process for removal of water and $CO_2$ from air in which an adsorbent bed containing a layer of alumina and a layer of 13X zeolite, or a single layer bed entirely of alumina, is regenerated by TSA using a gas temperature of around 100° C. in the downstream part, whereas the upstream part on which water is adsorbed is regenerated partly by TSA and partly by PSA. Such a process is known by the acronym TPSA. This process is run to $CO_2$ breakthrough from the end of the bed, and the ratio of heating time to online time required to desorb the $CO_2$ and water adsorbed on the bed is 46% and 35% in Examples 2 and 3 respectively.

PCT/EP2012/060317 describes a method of removal of nitrous oxide, carbon dioxide and water from a feed air stream in which method the feed air stream is passed through a first adsorbent having a Henry's Law selectivity for $CO_2$ over $N_2O$ of at least 12.5 and a second adsorbent, occupying from 25% to 40% by volume of the total volume of the first and second adsorbents, whose Henry's Law constant for the adsorption of $CO_2$ is less than 1020 mmol/g/atm and whose Henry's Law selectivity for $CO_2$ over $N_2O$ is at most 5, in which the regeneration of the adsorbents is by means of a first regeneration gas having a temperature of between 20° C. and 80° C. and 10° C. to 60° C. higher than the feed gas temperature and subsequently a second regeneration gas having a lower temperature than the first regeneration gas.

WO2005/000447 describes a process in which the use of an adsorbent through which radial flow patterns are provided allows a reduction of the cycle time for a TSA process for the removal of $CO_2$ and $H_2O$ from an air feed stream, and also the reduction of heat losses and thus increased efficiency of the process. The use of a radial bed is important in preventing loss of heat to the external parts of the adsorbent vessel.

CA804391 relates to a process of drying air, and teaches that a dessicant bed can be used efficiently despite fluctuations in the level of moisture in the feed air by monitoring the position of the water adsorption front within the bed and regenerating the bed once the front has reached a chosen position within the bed.

It is known that, in certain locations, the ambient level of $CO_2$ present in air has increased considerably compared with the levels that prior art processes have needed to address. For example, where an air separation plant is located in an area where there is heavy industry, it is frequently the case that an elevated level of $CO_2$ will be observed in the air.

The selectivity exhibited by an adsorbent for one gas compared with that for another gas can be expressed as the ratio of the Henry's Law constants (initial isotherm slopes) for the two gases at 30° C.

The present invention aims to provide a method of removal of high levels of water, carbon dioxide and nitrous oxide, and preferably also hydrocarbons such as propane, ethylene, propylene, acetylene and/or butane, present in ambient air. In particular, it is an aim of the present invention to provide higher levels of $N_2O$ removal than are obtained in the processes described in U.S. Pat. No. 584,295, U.S. Pat. No. 5,614,000, U.S. Pat. No. 5,855,650 and WO2005/000447. Without the use of CaX as the final adsorbent layer, if TSAs in the literature are run, as taught, to $CO_2$ breakthrough, then $N_2O$ removal will be less than 30-70% depending on operating conditions and bed layering schemes.

It is a further aim of the present invention to provide a method whereby the level of breakthrough of the nitrous oxide and, where present, hydrocarbons is related to the carbon dioxide level within the adsorbent, such that ensuring that the carbon dioxide level at a chosen point in the adsorbent bed is below a desired threshold ensures that the level of the nitrous oxide, and, where present, hydrocarbons, is also below a desired threshold.

It is a further aim of the present invention to provide a more economical method of treating large volumes of air per unit volume of bed than is provided in PCT/EP2012/060317.

It is a further aim of certain embodiments of the present invention to reduce the ratio of heating time to online time compared with prior art processes using thermal regeneration of at least part of the adsorbent bed.

It is a further aim of the present invention to avoid the use of highly water-sensitive adsorbents such as CaX. As the capacity of CaX is a very strong function of water loading, the use of this adsorbent requires great care to be taken in loading and operation to ensure that it does not come into contact with water, particularly where a steam heater is used to supply the heated regenerating gas. Further, as temperatures above 220° C. are used to regenerate CaX in order to remove any adsorbed water, the avoidance of this adsorbent allows the use of an electric heater in addition to the steam heater to be avoided.

It is an aim of the present invention to allow an existing plant set up for TSA using a three-layer bed for removal of $H_2O$, $CO_2$ and $N_2O$ to be upgraded to provide $N_2O$ removal without use of CaX and without needing to increase the size of the adsorbent bed.

It is a further aim of certain embodiments of the present invention to reduce the molar purge to air ratio used, i.e. to reduce the quantity of regeneration gas required compared to the quantity of feed gas supplied during the on-line time for the adsorbent bed, compared with those typical of PSA or TEPSA processes.

It is a yet further aim of certain embodiments of the invention to provide a method of determining conditions under which the removal of $N_2O$, $CO_2$ and water can be conducted with a given set of adsorbents to ensure a desired degree of removal of $CO_2$, $N_2O$ and $H_2O$.

It is a yet further aim of certain embodiments of the present invention to provide a range of operating conditions allowing the onstream time for the adsorbent bed to be extended, thus reducing switch losses, and/or reducing the required regeneration flow rate.

It is a further aim of certain embodiments of the present invention to provide an upgrade to existing apparatus in order that it can provide improved nitrous oxide removal.

It is a further aim of the present invention to provide apparatus and conditions under which elevated levels of $CO_2$ and/or $N_2O$ present in a feed air stream can be removed.

BRIEF SUMMARY

The present inventors have sought to provide conditions under which removal of $CO_2$ and water from a feed air stream, plus reduction by a desired degree of the level of $N_2O$ in that feed air stream, can be achieved without the use of highly water sensitive and expensive adsorbents and without incurring high switch losses or requiring excessively high regeneration temperatures. With this aim in mind, the inventors set out to determine whether efficient conditions could be achieved for the reduction of the levels of $CO_2$, $N_2O$ and water on a bed having a first adsorbent such as alumina and a second adsorbent such as 13X. To do so is contrary to the teachings of, for example, EP0992274, which teaches that a third layer of an adsorbent having a high $N_2O/CO_2$ selectivity, such as CaX, in addition to the first two adsorbents, is required in order that nitrous oxides can be removed.

Referring to FIG. 1, the present inventors have determined the breakthrough curves for nitrous oxide and carbon dioxide on an adsorbent bed comprising 320 mm alumina and 705 mm 13X, using a feed concentration of 500 ppm $CO_2$ and 320 ppm $N_2O$. The analysers measuring $CO_2$ and $N_2O$ concentration were placed at the exit (i.e. the downstream end) of the 13X bed. It can be seen that, if this adsorbent remains online until breakthrough of carbon dioxide (1 ppm) at about 390 min, as taught in the prior art, one would expect a concentration of $N_2O$ exiting the bed of at least 475 ppb, which is a greater breakthrough concentration than the feed concentration, as carbon dioxide, when co-adsorbing with nitrous oxide, is known to displace already adsorbed $N_2O$, causing a high concentration pulse of $N_2O$ to leave the bed immediately prior to $CO_2$ breakthrough.

The present inventors have realised that if space is provided in the 13X for adsorption of $N_2O$ alone, this displacement by $CO_2$ does not occur, and so both $CO_2$ and $N_2O$ can efficiently be removed on 13X, and the mass transfer characteristics of the two adsorbates can be modelled as if the two are adsorbed independently. When the quantity of 13X that would be required to adsorb 95% of the expected $N_2O$ in a typical feed air stream was calculated from known adsorbent capacities and parameters and compared with the amount of CaX required for the same purpose, it is found that for this particular set of process conditions, the volume of 13X provided for $N_2O$ adsorption alone should be approximately twice that of CaX provided in prior art apparatus according to EP0992274. One can therefore calculate the required proportions of alumina and 13X (or alternative suitable adsorbents as defined below) to remove the desired degree of water, carbon dioxide and nitrous oxide, based on the expected feed concentrations of those components and the intended online time of the apparatus, by calculating the amount of alumina plus 13X needed to remove all water (on the alumina only) and 99% of the $CO_2$ (on alumina and 13X), and then adding the quantity of 13X calculated to be required to remove the desired amount of $N_2O$.

The present inventors then faced the problem of determining when the adsorbent bed would need to be regenerated, i.e. the point at which the desired maximum concentration of $N_2O$ breaking through the bed would be exceeded. Typically, prior art methods are run to $CO_2$ breakthrough from the bed, which is not practical here as explained above. Measurement of $N_2O$ breakthrough would be possible, but impractical to do accurately given the much smaller concentration of $N_2O$ present in the feed air stream (ppb concentration rather than ppm). At the desired level of $N_2O$ removal, the $CO_2$ concentration breaking through the bed would be zero or very small (see for example FIG. 1 at 240 min), and thus it is not practical to determine the online time based on a $CO_2$ exit concentration either. Therefore, the present inventors decided to monitor $CO_2$ concentration at a chosen position within the adsorbent bed, by correlating the maximum desired $N_2O$ concentration at the outlet of the bed with the $CO_2$ concentration at the chosen position within that bed. The online time can then be determined by detection of the correlated $CO_2$ concentration by the analyser within the adsorbent bed. The correlation of the $CO_2$ concentration and $N_2O$ concentration can be determined by placing an analyser for $CO_2$ within the adsorbent bed, and an analyser for $N_2O$ at the exit of the adsorbent bed, and relating the concentration measured by each analyser at a given online time. Alternatively, the online time for a given adsorbent bed can be selected based on the $N_2O$ breakthrough level given in a study such as that depicted in FIG. 1, and a $CO_2$ analyser can be placed within the bed and the concentration detected by that analyser at the end of the online time determined. A suitable $CO_2$ analyser position can be deduced from the expected relative amounts of the adsorbents likely to be occupied by $CO_2$ and $N_2O$, based on the breakthrough curves for the given system, such as in FIG. 1.

In a first aspect, the present invention provides a method for determining conditions for the reduction, prior to cryogenic distillation, of the level of water, carbon dioxide and nitrous oxide in a feed air stream in a process comprising:

(a) passing said feed air stream at a feed pressure in a feed direction through a first adsorbent which
has a Henry's Law selectivity for carbon dioxide over nitrous oxide measured at 30° C. of at least 12.5,
and subsequently through a second adsorbent whose Henry's Law constant for the adsorption of $N_2O$ measured at 30° C. is less than 500 mmol/g/atm and whose Henry's Law selectivity for $CO_2$ over $N_2O$ is at most 5;

(b) ceasing to pass said feed air stream to said first and second adsorbents after a first time period;

(c) depressurising the gas in contact with the first and second adsorbents to a second pressure less than the feed pressure;

(d) passing regenerating gas at the second pressure and at a first temperature which is in the range 140 to 220° C. to at least the second adsorbent in a direction opposite to the feed direction for a second time period, and subsequently passing the regenerating gas at the second pressure and a second temperature less than the first temperature to the second and first adsorbents in a direction opposite to the feed direction for a third time period;

(e) ceasing passing regenerating gas to the first and second adsorbents;

(f) repressurising the gas in contact with the first and second adsorbents to the feed pressure;

(g) repeating steps (a) to (f);
wherein the first adsorbent occupies from 25% to 40% by volume of the total volume occupied by the first and second adsorbents; and
wherein the molar ratio of the regenerating gas to the feed air supplied during each iteration of the steps (a) to (f) is from 0.08 to 0.5;
which method comprises:
(i) placing an analyser for $CO_2$ concentration measurement at a chosen position within the length of the second adsorbent;
(ii) determining the threshold concentration measured by the $CO_2$ analyser when a desired maximum level of $N_2O$ is simultaneously obtained at the downstream end of the second adsorbent in the feed direction;
(iii) using the result of step (ii) to determine the maximum duration of the first time period, such that the maximum duration of the first time period is the time taken from commencing passing the feed air stream to the first and second adsorbents to the measurement by the analyser of the determined threshold concentration of $CO_2$.

In a second aspect, the present invention provides a process for the reduction of the level of water, carbon dioxide and nitrous oxide in a feed air stream prior to cryogenic distillation, comprising:
(a) passing said feed air stream at a feed pressure in a feed direction through a first adsorbent which has a Henry's Law selectivity for carbon dioxide over nitrous oxide measured at 30° C. of at least 12.5, and subsequently through a second adsorbent whose Henry's Law constant for the adsorption of $N_2O$ measured at 30° C. is less than 500 mmol/g/atm and whose Henry's Law selectivity for $CO_2$ over $N_2O$ is at most 5;
(b) ceasing to pass said feed air stream to said first and second adsorbents after a first time period;
(c) depressurising the gas in contact with the first and second adsorbents to a second pressure less than the feed pressure;
(d) passing regenerating gas at the second pressure and at a first temperature which is in the range 140 to 220° C. to at least the second adsorbent in a direction opposite to the feed direction for a second time period, and subsequently passing the regenerating gas at the second pressure and a second temperature less than the first temperature to the second and first adsorbents in a direction opposite to the feed direction for a third time period;
(e) ceasing passing regenerating gas to the first and second adsorbents;
(f) repressurising the gas in contact with the first and second adsorbents to the feed pressure;
(g) repeating steps (a) to (f);
wherein the first adsorbent occupies from 25% to 40% by volume of the total volume occupied by the first and second adsorbents;
wherein the method further comprises:
(i) placing an analyser for $CO_2$ concentration measurement at a chosen position within the length of the second adsorbent; and
(ii) determining the threshold concentration measured by the $CO_2$ analyser when a desired maximum level of $N_2O$ is simultaneously obtained at the downstream end of the second adsorbent in the feed direction;
wherein the maximum duration of the first time period is the time taken from commencing passing the feed air stream to the first and second adsorbents to the measurement by the analyser of the determined threshold concentration of $CO_2$; and
wherein the molar ratio of the regenerating gas to the feed air supplied during one iteration of the steps (a) to (f) is from 0.08 to 0.5.

The first adsorbent and the second adsorbent may be provided in separate vessels, but preferably are provided as, respectively, upstream and downstream (with respect to the feed direction) layers of a single bed of adsorbent.

Suitably, the first time period is equal to the time taken from commencing passing the feed air stream to the first and second adsorbents to the measurement by the analyser of the determined threshold concentration of $CO_2$.

The method and process comprise measuring the concentration of $CO_2$ at a chosen point within the adsorbent bed, which chosen point is upstream of the exit of the bed. This ensures that a desired degree of $N_2O$ and $CO_2$ removal is obtained by monitoring only the $CO_2$ concentration rather than the (significantly lower) $N_2O$ concentration. The monitoring point is chosen to ensure that, at the detected $CO_2$ threshold, there is sufficient capacity in the remaining zeolite downstream of the monitoring point to adsorb the amount of $N_2O$ required to obtain the desired degree of $N_2O$ removal. This permits efficient $N_2O$ and $CO_2$ removal without the use of an increased adsorbent volume (allowing a plant upgrade without increasing the bed size) compared with conventional three-layer bed TSA systems intended for the removal of $N_2O$, $CO_2$ and water from a feed air stream, and without the use of expensive and highly water-sensitive adsorbents such as CaX to remove the $N_2O$.

The conditions under which the method is conducted are selected such that the desired degree of removal of water, $CO_2$ and $N_2O$ is obtained while making the most efficient possible use of the adsorbent. These conditions vary depending on the feed concentration of $CO_2$ and $N_2O$. In general, a $CO_2$ feed concentration of 100-600 ppm, such as 300-500 ppm is considered typical, accompanied by an $N_2O$ feed concentration of about 0.3 ppm. However, it has recently been noted that in some locations $CO_2$ feed concentrations of 400-1000 ppm, such as 400-600 ppm are typical, accompanied by $N_2O$ feed concentrations of 300-800 ppb, such as 300-600 ppb. The conditions under which the method of the present invention is conducted can be adapted to allow for these differing feed concentration ranges of $CO_2$ and $N_2O$ such that a desired low content of both of these components can be obtained downstream of the adsorbents.

A suitable position for the analyser can be determined, as explained above, by reference to the breakthrough curves for $CO_2$ and $N_2O$ on the adsorbents and under the conditions of interest. For example, using FIG. 1, one can see that if the bed is run to $CO_2$ breakthrough (ca 390 min) the whole of the bed is used for $CO_2$ adsorption; if the bed is online for only 180 min, then around 45% of the bed is used for $CO_2$ removal and the remaining 55% is available to remove 95% of the feed $N_2O$. Thus, the analyser can be positioned at or close to the expected boundary between the volume of the bed intended for $CO_2$ adsorption and that for $N_2O$ adsorption, although this will also to some extent depend on the concentration of $CO_2$ it is intended to detect using the analyser; a higher concentration will be detected further upstream of the boundary point. Suitably, the chosen position of the analyser for $CO_2$ within the length of the second adsorbent is at a distance up to 50%, preferably up to 45%, such as 41% of the way along the length of the second adsorbent in a downstream direction when the bed is online.

Suitably, once a selected maximum $CO_2$ concentration is reached, the first and second adsorbents are regenerated. Suitably, the selected maximum $CO_2$ concentration is 200 ppm, preferably 100 ppm, and more preferably 20 ppm, such as 1 ppm; as a practical matter the concentration of $CO_2$ must be at least 20 ppb in order to be detected. These values are instantaneous $CO_2$ concentrations.

In a particular embodiment, the present invention provides a process for the reduction of the level of water, carbon dioxide and nitrous oxide in a feed air stream prior to cryogenic distillation, comprising:

(a) passing said feed air stream at a feed pressure in a feed direction through a first adsorbent which
has a Henry's Law selectivity for carbon dioxide over nitrous oxide measured at 30° C. of at least 12.5,
and subsequently through a second adsorbent whose Henry's Law constant for the adsorption of $N_2O$ measured at 30° C. is less than 500 mmol/g/atm and whose Henry's Law selectivity for $CO_2$ over $N_2O$ is at most 5;
(b) ceasing to pass said feed air to said first and second adsorbents after a first time period;
(c) depressurising the gas in contact with the first and second adsorbents to a second pressure less than the feed pressure;
(d) passing regenerating gas at the second pressure and at a first temperature which is in the range 140 to 220° C. to at least the second adsorbent in a direction opposite to the feed direction for a second time period, and subsequently passing the regenerating gas at the second pressure and a second temperature less than the first temperature to the second and first adsorbents in a direction opposite to the feed direction for a third time period;
(e) ceasing passing regenerating gas to the first and second adsorbents;
(f) repressurising the gas in contact with the first and second adsorbents to the feed pressure;
(g) repeating steps (a) to (f);
wherein the first adsorbent occupies from 25% to 40% by volume of the total volume occupied by the first and second adsorbents;
wherein the maximum duration of the first time period is the length of time taken from commencing passing the feed air stream to the first and second adsorbents to the detection of 1 ppm $CO_2$ at a point up to 45% of the way along the length of the second adsorbent in the feed direction; and
wherein the molar ratio of the regenerating gas to the feed air supplied during one iteration of the steps (a) to (f) is from 0.08 to 0.5.

In the particular embodiment above, using an analyser that detects 1 ppm $CO_2$, it is possible to remove 95% of the $N_2O$ from the feed air stream when the analyser is present at 43% of the way along the second adsorbent; to remove 96% when the analyser is 41% of the way along the second adsorbent, to remove 97% when the analyser is 38% of the way along the second adsorbent, to remove 98% when the analyser is 35% of the way along the adsorbent and 99% when the analyser is up to 27% of the way along the adsorbent.

The skilled person is able to deduce the required position of the analyser to obtain the desired degree of nitrous oxide removal where an analyser detects a different carbon dioxide concentration. Alternatively, the position of the analyser can be kept at a chosen position within the bed, and the $N_2O$ breakthrough level controlled by alteration of the threshold level of $CO_2$ detected by the analyser that triggers the regeneration of the bed; for a given analyser position, the higher the threshold concentration of $CO_2$ that must be detected by the analyser to trigger regeneration of the bed, the higher the level of $N_2O$ breakthrough from the bed will be. This can be tailored to give an acceptable $N_2O$ content of the air downstream of the adsorbent for a given purpose of the treated air.

Alternatively, the measurement of $CO_2$ concentration can be monitored from time to time only, rather than for every period of time for which the feed air stream is passed to the adsorbents, to set a fixed time for which the feed air stream is passed to the first and second adsorbents prior to regeneration, which fixed time is reviewed and altered if necessary in response to a subsequent measurement of $CO_2$ concentration.

In order to ensure that $N_2O$ and $CO_2$ levels at the outlet of the second adsorbent remain below required levels based on a measurement of the $CO_2$ level at a chosen point within the adsorbent bed, the properties of the first and second adsorbents with respect to the three components $H_2O$, $CO_2$ and $N_2O$ must be balanced to ensure that $N_2O$ breakthrough does not occur before the measured $CO_2$ level exceeds the chosen threshold value. On a given adsorbent, the speed at which a component of the feed air stream moves through the bed is dependent on its strength of adsorption. Of water, $CO_2$ and $N_2O$, water is the most strongly adsorbed on alumina or zeolites, and thus moves very slowly through the adsorbent bed. $CO_2$ is less strongly adsorbed than water, but, on the adsorbents used in the present invention, more strongly adsorbed than $N_2O$. It is desired that at least some of the $CO_2$, as well as all of the $H_2O$, present in the feed air stream is adsorbed on the first adsorbent, and that the second adsorbent is used for the adsorption of $N_2O$ and the remaining $CO_2$, as well as any hydrocarbons present in the feed air stream. Preferably, the first adsorbent is capable of adsorbing at least 99% of the water present in the feed air stream as well as 10-60% of the $CO_2$, and more preferably 20-40% of the $CO_2$, present in the feed air stream. That being so, a first adsorbent having a high capacity for $CO_2$ and $H_2O$, and a Henry's Law selectivity for $CO_2$ over $N_2O$ measured at 30° C. of at least 12.5, is preferably used. This allows $N_2O$ to travel rapidly through the first adsorbent as it is not strongly adsorbed thereon, and, it is believed, prevents $CO_2$ from displacing a pulse of $N_2O$ on breakthrough from the first adsorbent as insufficient $N_2O$ is adsorbed thereon for any pulse to cause a problematically high outlet concentration after the second adsorbent. Further, the first adsorbent must be capable of desorbing $H_2O$ and $CO_2$ under PSA conditions.

Preferably, said first adsorbent comprises activated alumina, as this adsorbent has a high water capacity, thus preventing water from coming into contact with the usually more water sensitive second adsorbent, and can simultaneously adsorb water and carbon dioxide by formation of bicarbonates on the alumina surface. More preferably, said first adsorbent comprises activated alumina impregnated with alkali and/or alkaline earth metal carbonates, bicarbonates, hydroxides and/or phosphates. Preferably, the activated alumina is impregnated with potassium carbonate. The impregnated alumina may be as described in U.S. Pat. No. 5,656,064 in which a starting alumina is treated with a basic solution having a pH of at least 9, e.g. a solution of $KHCO_3$, and drying at a temperature which is low enough (e.g. below 200° C.) to avoid decomposing the impregnant compound to a form which adsorbs $CO_2$ in such a manner that the compound does not regenerate under the intended regeneration conditions. Preferably, the pH of the impregnating solution is related to the zero point charge (ZPC) of the alumina according to the formula: pH≥ZPC−1.4, or more preferably: ZPC+2≥pH≥ZPC−1.4. Alternatively, the impregnated alumina may be as described in U.S. Pat. No. 7,759,288, which is made by physically mixing the alumina and the impregnant compound rather than an aqueous impregnation process. The impregnant is preferably an alkali metal or ammonium hydroxide, carbonate, bicarbonate, phosphate or organic acid salt. More preferably, the impregnant is selected from the group consisting of $K_2CO_3$, $Na_2CO_3$, $KHCO_3$, $NaHCO_3$, NaOH and KOH. It is found that such impregnated aluminas have enhanced $CO_2$ uptake but that their capacity with respect to nitrous oxide is similar to that of unimpregnated aluminas.

Preferably, the first adsorbent has a BET surface area of 400 m²/g or less. It is preferred that the first adsorbent has a relatively low surface area in order that water and $CO_2$ can be desorbed under PSA conditions.

Preferably, said first adsorbent layer comprises from 25% to 40% by volume, such as from 25% to less than 40% by volume, and more preferably 28% to 37% of the total volume of the first and second adsorbents, such as 31 or 32%.

The second adsorbent is provided in a quantity sufficient to adsorb the $N_2O$, and optionally also any hydrocarbon impurities, present in the feed air stream, plus sufficient carbon dioxide that the carbon dioxide level at a chosen point in the adsorbent bed reaches a chosen threshold before the concentration of nitrous oxide and, if present, the hydrocarbon impurities, breaking through the bed exceeds a chosen value. The second adsorbent is selected to have a high capacity for $N_2O$, and optionally also for the hydrocarbon impurities, in order that the size of the layer can be kept as small as possible, which is advantageous for reasons of cost, as the second adsorbent is generally significantly more expensive than the first adsorbent. The second adsorbent comprises from 60% to 75% by volume of the total volume of the first and second adsorbents, preferably 65% to 72% by volume, with lower values within each range generally being preferred for reasons of cost, where the $N_2O$ removal level of a given range is within acceptable limits for the intended application.

The second adsorbent has higher adsorption capacity for both $CO_2$ and $N_2O$ than the first adsorbent at the feed conditions.

The second adsorbent must also be able to desorb the $N_2O$, and where applicable also the hydrocarbon impurities, effectively under the chosen regeneration conditions. The present inventors have sought to provide a process that can function at a moderate regeneration temperature in order that the cost in terms of providing heaters in the apparatus and in terms of the power usage can be kept to a minimum. This requires the capacity of the second adsorbent for carbon dioxide to be balanced against the desired regeneration temperature to be used. If $CO_2$ and/or $N_2O$ is adsorbed too strongly on the second adsorbent, the second adsorbent will not be regenerated sufficiently at the chosen regeneration conditions. It has been found by the present inventors that CaX, taught for $N_2O$ removal under TSA regeneration at high temperatures, while having a high $N_2O$ capacity, is not able to desorb the $N_2O$ and $CO_2$ effectively under the preferred regeneration conditions of the present invention if it is contaminated with water. It has been found by the present inventors that an aggregated zeolitic adsorbent based on an LSX zeolite or X zeolite, whether or not binderless, is suitable for use as the second adsorbent in the present invention. Said second adsorbent has a Henry's Law constant for adsorption of $N_2O$ measured at 30° C. of less than 500 mmol/g/atm. The present inventors have also found that alumina is not suitable for use as the second adsorbent, and therefore the second adsorbent has a maximum Henry's Law selectivity for $CO_2/N_2O$ measured at 30° C. of 5, and, preferably, a Henry's Law constant for adsorption of $CO_2$ measured at 30° C. of greater than 5.6 mmol/g/atm. Preferably, said second adsorbent is selected from bound or binderless: NaX having a Si/Al ratio of from 1.25 to 1.0, 4A zeolite, 5A zeolite, mordenite, chabazite and clinoptilolite; more preferably, said second adsorbent is selected from bound or binderless: NaX having a Si/Al ratio of from 1.25 to 1.0, 4A zeolite, and 5A zeolite; and most preferably said second adsorbent is selected from bound or binderless: NaX having a Si/Al ratio of from 1.25 to 1.0, such as 13X zeolite or NaLSX, and 5A zeolite. The most preferred adsorbents are relatively low cost and have a good $N_2O$ capacity under the conditions used in the present invention.

The Henry's Law constants have been measured at 30° C. for a number of adsorbents for $N_2O$ and $CO_2$, the Henry's Law selectivity for $CO_2$ compared with $N_2O$ calculated, and the BET surface areas determined, as set out in Table 1 below:

TABLE 1

| Adsorbent | $K_H CO_2$ (mmol/ g/atm) | $K_H N_2O$ (mmol/ g/atm) | Selectivity $CO_2/N_2O$ | Selectivity $N_2O/CO_2$ | BET surface area (m²/g) |
|---|---|---|---|---|---|
| Axen AA-300 alumina | 5.6 | 0.45 | 12.5 | 0.08 | 320 |
| UOP 13X | 162 | 63 | 2.57 | 0.39 | 726 |
| UOP 5A | 145 | 54 | 2.69 | 0.37 | 540 |
| Binderless CaX | 1031 | 1035 | 1.00 | 1.00 | 742 |
| Na-mordenite | 366 | 185 | 1.98 | 0.51 | 421 |
| Ca-mordenite | 374 | 113 | 3.31 | 0.30 | 448 |
| CaX | 1020 | 503 | 2.03 | 0.49 | 712 |
| $K_2CO_3$-impregnated alumina (Axen AA-320) | 22.8 | 0.42 | 54.3 | 0.018 | 260 |
| NaLSX | 310 | 102 | 3.04 | 0.33 | 712 |

It can be seen that both aluminas in the table above satisfy the preferred selectivity and surface area constraints for the first adsorbent, and that all of the adsorbents except CaX, binderless CaX and alumina satisfy the preferred $K_H CO_2$ and Henry's law selectivity for $CO_2/N_2O$ constraints for the second adsorbent.

As has been explained above, it is possible to determine the online time suitable for obtaining the desired degree of $N_2O$ removal by reference to the adsorption behaviour of $CO_2$ and $N_2O$ under the chosen conditions and the chosen position of the analyser within the second adsorbent bed.

Suitably, the time for which the feed air stream is passed to the first and second adsorbents prior to regeneration is from 100 min to 350 min, such as from 100 min to 300 min, such as from greater than 100 min to less than 250 min, preferably from 120 min to 240 min, such as from greater than 120 min to less than 200 min, for example 180 min. Suitably, the feed air stream is passed to the first and second adsorbents at a feed temperature of from 5° C. to 50° C., preferably from 10° C. to 30° C. Suitably, the feed pressure is from 1 bara (100 kPa) to 30 bara (2000 kPa), preferably from 4 bara (400 kPa) to 7 bara (700 kPa).

Preferably, the ratio of the time for which heated gas is passed to the adsorbent bed during regeneration (the heating time, or hot purge time, or second time period) to the online time (first time period) for the adsorbent bed is less than 35%. Where the feed $CO_2$ concentration is within a normal range, the ratio is preferably 30% or less, such as 25%. This allows a lower heat time to online time ratio than is observed in prior art processes for the removal of normal levels of $CO_2$ and water, and thus provides an energy saving. However, for higher feed $CO_2$ concentrations, a higher ratio close to 35% is preferred.

Periodic regeneration preferably takes place while a second set of the first and second adsorbents is used to continue the purification process, each set of the two adsorbents being on-line in the purification process and being regenerated in alternation.

Preferably, the regeneration of the first and second adsorbents comprises passing heated regeneration gas (purge gas) countercurrently through the second and first adsorbents for a period of from 20 min to 100 min, preferably 25 min to 80 min. The temperature of the heated gas is from 140° C. to 220° C., such as from greater than 140° C. to less than 200° C., preferably from 140° C. to 180° C., such as from greater than 140° C. to less than 160° C., or from greater than 150° C. to 200° C. Subsequently, the regeneration comprises passing a second regenerating gas at a temperature within the range given above for the feed temperature, but cooler than that of the heated gas temperature used, countercurrently through the second and first adsorbents. Preferably, the second regenerating gas has a temperature not more than 5° C. higher than the feed temperature. Suitably, the second regenerating gas may be passed to the adsorbents for a period of from 50 to 220 min, preferably from 80 to 180 min. Regeneration gas must not contain water, carbon dioxide, nitrous oxide, or, where hydrocarbons are to be removed from the feed air stream, hydrocarbons, and may suitably consist of $N_2$, $O_2$, CO, Ar, He, product air depleted in water and $CO_2$, and mixtures thereof. In a preferred embodiment, the regeneration gas would consist either of product $N_2$ or more preferably waste effluent from the $N_2$ plant (60% $O_2$/40% $N_2$). Preferably, the regeneration conditions selected result in regeneration of the second adsorbent by purge with the heated gas, that is, in a TSA type process, and regeneration of the first adsorbent by purge with the cooler gas, that is, in a PSA-type process, as this ensures sufficient desorption of $CO_2$ and $N_2O$ from the second adsorbent to result in an acceptable working capacity while minimising the energy requirements of the desorption, as alumina may be regenerated effectively under PSA conditions. However, if desired, the first adsorbent may also be wholly or partially regenerated by purge with the heated gas in a TSA type process. This allows the adsorbent to be totally "cleaned" of all adsorbed air components, which may periodically be desirable. This can also be used as a means to recover $CO_2$ and/or $N_2O$ capacity in the event of an early impurity breakthrough from the adsorbent.

Suitably, the molar ratio of regenerating gas to feed gas is from 0.08 to 0.5, preferably from 0.1 to 0.3, more preferably from 0.2 to 0.25. A shorter heating time correlates with use of a higher molar ratio of regenerating gas to feed gas, as is known to the skilled person.

Suitably, at least 75% of the N2O present in the feed air is removed by the method of the present invention, preferably at least 80% or at least 90% and more preferably 95%, yet more preferably 96%, 97% or 98% and most preferably 99%. That is, the $N_2O$ level is preferably reduced to at most 25% of its original level in the feed air stream, preferably at most 20%, more preferably 10% and yet more preferably at most 5%, 4%, 3%, 2% and most preferably 1%.

Where the feed air stream further comprises at least one hydrocarbon selected from the group consisting of ethylene, acetylene, butane, propylene and propane, the level of said at least one hydrocarbon is reduced by adsorption on the second adsorbent. Preferably, at least 60% of the or at least one hydrocarbon is removed by the method of the present invention, and preferably at least 75%, such as at least 85% and more preferably 90%. It has been found by the present inventors that the hydrocarbon(s) coadsorb on the second adsorbent with the $CO_2$ and $N_2O$ and that no additional second adsorbent need be provided to accommodate the hydrocarbon(s).

Suitably, the process further comprises a step of conducting cryogenic distillation of the purified air stream to separate a nitrogen-rich stream and/or an oxygen-rich stream.

In a third aspect, the present invention provides an apparatus for the reduction of the level of water, carbon dioxide and nitrous oxide from a feed air stream prior to cryogenic distillation, comprising:
in an adsorbent bed, a layer of a first adsorbent which has a Henry's Law selectivity for carbon dioxide over nitrous oxide measured at 30° C. of at least 12.5 and a second adsorbent whose Henry's Law constant for the adsorption of $N_2O$ measured at 30° C. is less than 500 mmol/g/atm and whose Henry's Law selectivity for $CO_2$ over $N_2O$ is at most 5, wherein the first adsorbent occupies from 25% to 40% by volume of the total volume occupied by the first and second adsorbents; an analyser for carbon dioxide placed within the length of the second adsorbent.

The apparatus used in the second aspect of the invention may suitably further comprise one or more of the following: an inlet to the adsorbent bed for feeding the feed air stream in a feed direction in contact with the adsorbents and an outlet for the feed gas, valves for controlling the flow of the feed air stream, valves for depressurising the gas in contact with the adsorbents to a lower pressure, an inlet to the adsorbent bed for supplying regeneration gas to the adsorbents in a direction opposite to the feed direction and an outlet for the regenerating gas, valves for controlling the flow of regenerating gas, a heater for raising the temperature of the regenerating gas, and a control system for controlling the valves and the heater. Suitably, the apparatus may be in accordance with that described with reference to FIG. 2 and FIG. 3.

In a fourth aspect, the present invention provides the use of an apparatus according to the third aspect of the invention for the removal of nitrous oxides from a feed air stream prior to cryogenic distillation.

In a fifth aspect, the present invention provides a method of upgrading an apparatus designed to reduce the levels of carbon dioxide, nitrous oxide and water from a feed air stream by a temperature swing adsorption process in order that it can provide a reduction in the level of nitrous oxide in the feed air stream without use of an adsorbent having a Henry's Law selectivity measured at 30° C. for nitrous oxide compared to carbon dioxide of 0.5 or more, such as CaX or binderless CaX, in which the adsorbents contained in the apparatus are removed and replaced with an identical total volume of adsorbent consisting of a layer of a first adsorbent which has a Henry's Law selectivity for carbon dioxide over nitrous oxide measured at 30° C. of at least 12.5 and a second adsorbent whose Henry's Law constant for the adsorption of $N_2O$ measured at 30° C. is less than 500 mmol/g/atm and whose Henry's Law selectivity for $CO_2$ over $N_2O$ is at most 5, wherein the first adsorbent occupies from 25% to 40% by volume of the total volume occupied by the first and second adsorbents, and in which an analyser for carbon dioxide is placed within the length of the second adsorbent.

All features described in connection with any aspect of the invention can be used with any other aspect of the invention.

BRIEF DESCRIPTION OF SEVERAL VIEWS OF THE DRAWINGS

The invention will be further described with reference to preferred embodiments and examples, and with reference to the drawings in which.

DETAILED DESCRIPTION

Figure 1:
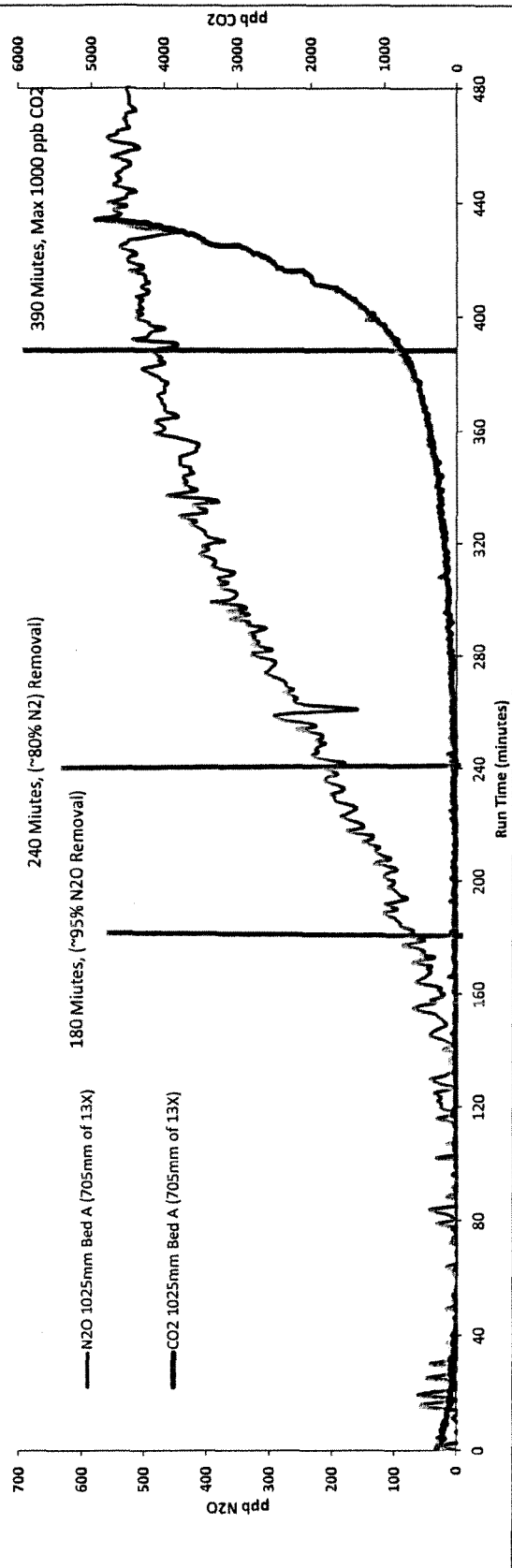
FIG. 1 shows breakthrough curves obtained on a 31% alumina/69% 13X adsorbent bad for $CO_2$ and $N_2O$ over a 480 min period.
Figure 2:
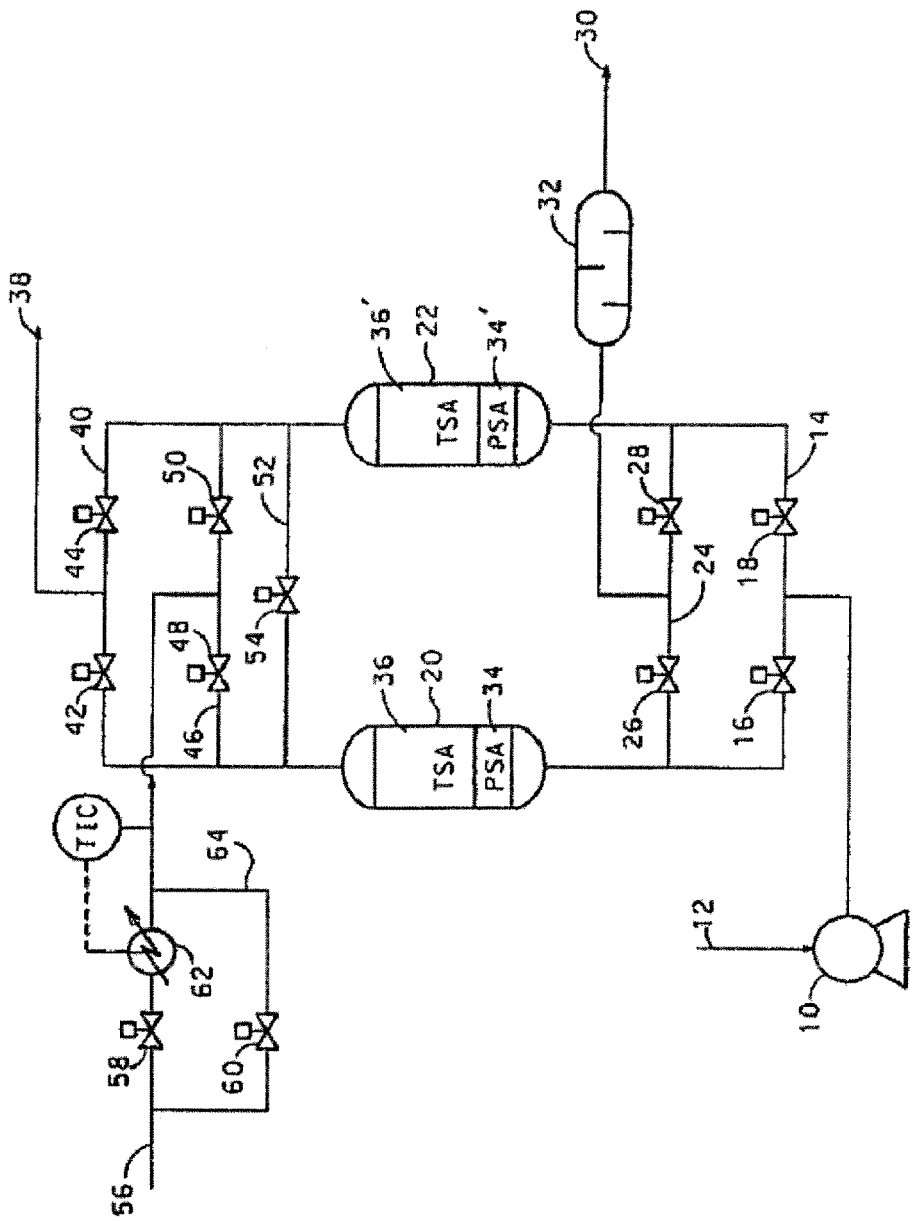
FIG. 2 shows an apparatus suitable for conducting the process of the present invention.

Referring to FIG. 2, this depicts schematically an apparatus suitable for use in the present invention. Air to be purified is supplied to a main air compressor system 10 at an inlet 12 in which it is compressed by a multi-stage compressor with inter and after cooling by heat exchange with water. The cooled compressed air is supplied to an inlet manifold 14 containing inlet control valve 16 and 18 to which is connected a pair of adsorbent bed containing vessels 20 and 22. The inlet manifold is bridged downstream of the control valves 16 and 18 by a venting manifold 24 containing venting valves 26, 28 which serve to close and open connections between the upstream end of respective adsorbent vessels 20 and 22 and a vent 30 via a silencer 32. Each of the two adsorbent beds 20 and 22 contains two adsorbents. The feed end adsorbent (i.e. that at the upstream or inlet manifold end of the bed) is designated by the numeral 34, 34' in respective beds and the product end adsorbent (i.e. that at the downstream or outlet manifold end of the bed) by the numeral 36, 36'.

The apparatus has an outlet 38 connected to the downstream ends of the two adsorbent vessels 20, 22 by an outlet manifold 40 containing outlet control valves 42, 44. The outlet manifold 40 is bridged by a regenerating gas manifold 46 containing regenerating gas control valves 48 and 50. Upstream from the regenerating gas manifold 46, a line 52 containing a control valve 54 also bridges across the outlet manifold 40.

An inlet for regenerating gas is provided at 56 which through control valves 58 and 60 is connected to pass either through a heater 62 or via a by-pass line 64 to the regenerating gas manifold 46.

The operation of the valves may be controlled by suitable programmable timing and valve operating means as known in the art, not illustrated.

In operation, air is compressed in the main air compressor system 10 and is fed to the inlet manifold 14 and passes through one of the two vessels containing adsorbent. Starting from a position in which air is passing through open valve 16 to adsorbent vessel 20, and through open valve 42 to the outlet 38, valve 18 in the inlet manifold will just have been closed to cut off vessel 22 from the feed of air for purification. Valve 44 will just have closed also. At this stage valves 48, 50, 54 and 26 are closed. Bed 20 is thus on line and bed 22 is to be regenerated.

Air to be purified enters the feed end of bed 20, and water and carbon dioxide from the air is adsorbed on to the adsorbent 34. The bed 20 is designed such that water will not be adsorbed on to the downstream adsorbent 36, as this adsorbent is a water-sensitive zeolite, and so the length of upstream adsorbent (alumina) 34 is selected such that the mass transfer zone for water never extends beyond the boundary between adsorbent 34 and adsorbent 36 during normal operation. Some of the $CO_2$ is to be adsorbed on the upstream adsorbent 34 also, and the remainder of the $CO_2$ will be adsorbed along with the $N_2O$ and any hydrocarbons on the downstream adsorbent 36. The concentration of $CO_2$ at a chosen distance along adsorbent 36 from the boundary with adsorbent 34 is measured, either at each on-line phase of bed 20, or from time to time to ensure that the time period for which the bed remains online results in an acceptable $N_2O$ breakthrough level. $CO_2$ does not break through the bed. Once the $CO_2$ concentration measured reaches a selected threshold, or the set time period has elapsed, the valve 16 is closed in order to shut off further feed air from passing through bed 20, and regeneration of the bed can commence as described for bed 22 below.

Regeneration of bed 22 takes place while bed 20 is online. To commence depressurisation of bed 22, valve 28 is opened and once the pressure in the vessel 22 has fallen to a desired level, valve 28 is kept open whilst valve 50 is opened to commence a flow of regenerating gas. The regenerating gas will typically be a flow of dry $CO_2$- and $N_2O$-free nitrogen obtained from the air separation unit cold box, possibly containing small amounts of argon, oxygen and other gases, to which the air purified in the apparatus shown is passed. Valve 60 is closed and valve 58 is opened so that the regenerating gas is heated to a temperature in the range of 140° C. to 220° C. before passing into the vessel 22. Although the regenerating gas enters the vessel 22 at the selected elevated temperature, it is very slightly cooled by giving up heat to desorb nitrous oxide and some of the carbon dioxide from the upper, downstream adsorbent portion 36' in the vessel. Since the heat pulse is retained in the system, the exit purge gas emerges from the vent outlet in a cooled state. Progressively, a heat wave moves through the upper adsorbent 36' as the nitrous oxide and, to some extent, the carbon dioxide is cleared. After a desired period, whilst the heat pulse is part way through the upper adsorbent 36', valve 58 is closed and valve 60 is opened so that the flow of regenerating gas now becomes cool. The cooled regenerating gas displaces the heat pulse further through the upper adsorbent 36'.

Whilst the upper adsorbent has been thus regenerated by TSA, the cool regenerating gas has continued to flow through the lower adsorbent and by virtue of its reduced pressure has desorbed water and carbon dioxide from the upstream adsorbent 34' by PSA. At the end of the allotted regeneration period, valve 50 may be opened to displace nitrogen from the adsorbent and, after the closing of valve 28, to repressurise the vessel 22 with purified air. Thereafter, valve 54 may be closed and valves 18 and 44 may be opened to put the vessel 22 back on line. Residual heat left in the bed may be removed by purified air as a temperature pulse which can be removed in a downstream heat exchanger. The vessel 20 may then be regenerated in a similar manner and the whole sequence continued with the vessels being online, depressurising, regenerating, repressurising and going back online in phased cycles of operation.

Figure 3:
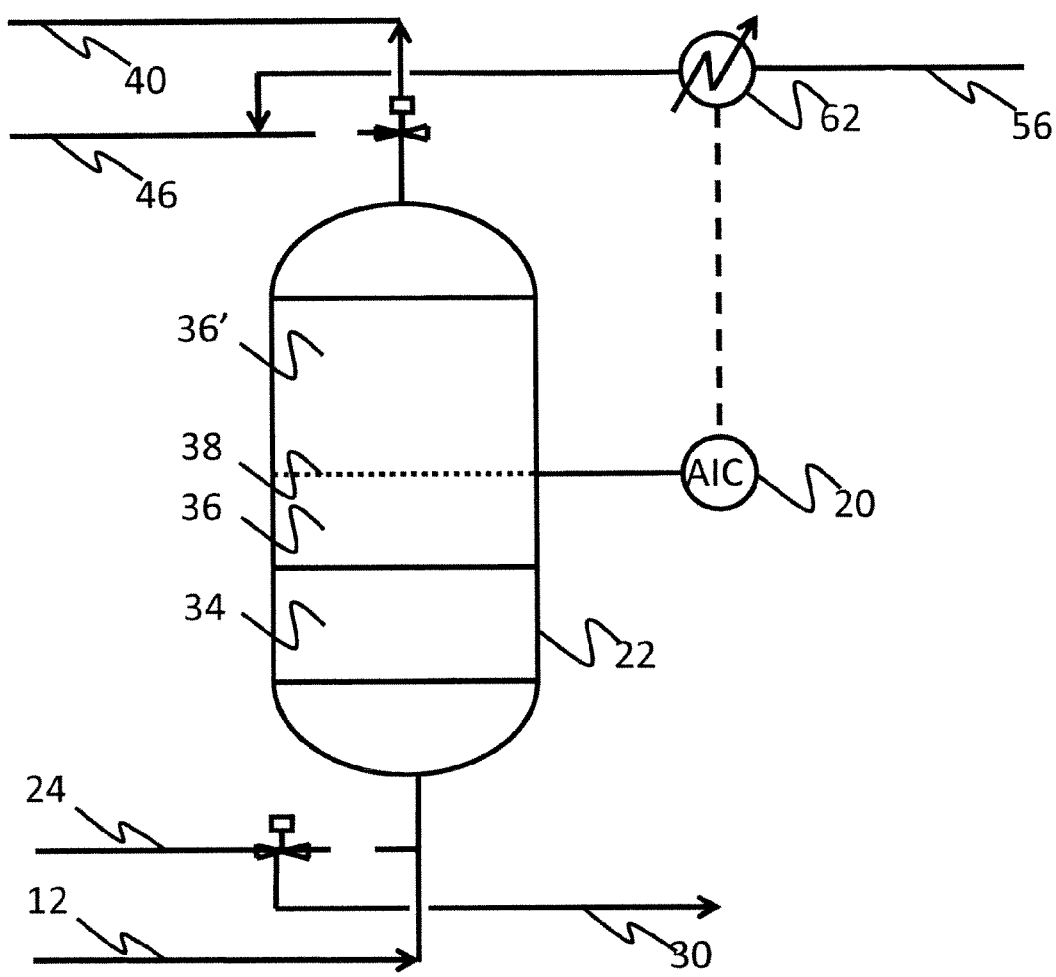
FIG. 3 shows in more detail the arrangement of the apparatus of FIG. 2 surrounding the adsorption bed.

FIG. 3 shows in greater detail the control strategy that ensures the removal of contaminants is at the desired level. Similarly to the description for FIG. 2, compressed air enters the vessel 22 via inlet piping 12 and goes through the first layer of adsorbent 34 and through the second layer of adsorbent 36, 36a before exiting the vessel through outlet pipe 40 which connects to the downstream part of the process.

The second layer of adsorbent, responsible for the removal of $CO_2$ and $N_2O$, can be divided into two subsections: 36, in which $CO_2$ and $N_2O$ are removed simultaneously according to the selectivity of the adsorbent, and 36a, in which only $N_2O$ is removed as the air stream is already free from $CO_2$. The dotted line 38 corresponds to the virtual separation of the two subsections, and to the bed height at which up to a chosen maximum level only of $CO_2$ may be detected by analyser 20 at any time while the bed is on line, ensuring an adequate level of $N_2O$ removal.

Suitable process conditions are set out in Table 2 below:

TABLE 2

| Process Conditions | Preferred | More Preferred |
| --- | --- | --- |
| Online time | 100 to 350 min | 120 to 240 min |
| Purge/Air ratio | 0.08 to 0.5 | 0.1 to 0.3 |

TABLE 2-continued

| Process Conditions | Preferred | More Preferred |
|---|---|---|
| Feed $CO_2$ Concentration | 300 to 1000 ppm | 400 to 700 ppm |
| Hot regeneration temperature | 140 to 220° C. | 140 to 180° C. |
| Feed temperature | 5 to 50° C. | 10 to 30° C. |
| Feed pressure | 1 to 30 bara | 4 to 7 bara |
| Hot purge duration | 20 to 100 min | 25 to 80 min |
| Feed $N_2O$ (ppb) | 200 to 600 | 300 to 400 |

Where the feed concentration of $CO_2$ is within a normal range, the preferred process conditions are set out in Table 3 below:

TABLE 3

| Process Conditions | Preferred | More Preferred |
|---|---|---|
| Online time | 100 to 250 min | 120 to 200 min |
| Purge/Air ratio | 0.1 to 0.5 | 0.1 to 0.3 |
| Feed $CO_2$ Concentration | 300 to 600 ppm | 400 to 500 ppm |
| Hot regeneration temperature | 140 to 220° C. | 140 to 160° C. |
| Feed temperature | 5 to 50° C. | 10 to 30° C. |
| Feed pressure | 1 to 30 bara | 4 to 7 bara |
| Hot purge duration | 20 to 70 min | 25 to 50 min |
| Feed $N_2O$ (ppb) | 200 to 600 | 300 to 400 |

Where the feed concentration of $CO_2$ is elevated, such as where an air separation plant is located close to plants that give out $CO_2$ and/or $N_2O$, the preferred process conditions are set out in Table 4 below:

TABLE 4

| Process Conditions | Preferred | More Preferred |
|---|---|---|
| Online time | 100 to 300 min | 140 to 240 min |
| Purge/Air ratio | 0.08 to 0.3 | 0.08 to 0.12 |
| Feed $CO_2$ Concentration | 300 to 1000 ppm | 400 to 600 ppm |
| Hot regeneration temperature | 140 to 220° C. | 120 to 180° C. |
| Feed temperature | 5 to 50° C. | 10 to 30° C. |
| Feed pressure | 1 to 30 bara | 4 to 7 bara |
| Hot purge duration | 20 to 100 min | 25 to 80 min |
| Feed $N_2O$ (ppb) | 200 to 600 | 300 to 400 |

Thus, one may employ a layered bed containing an upstream layer of alumina followed by a downstream layer of molecular sieve. The alumina section may be an enhanced alumina of the type which may be produced by impregnating approximately 5% to 10% by weight potassium carbonate on the alumina by treating the starting alumina with a potassium carbonate solution and drying at high temperatures of up to about 125° C. Such aluminas have a particularly high capacity for carbon dioxide.

It will of course be understood that the vessels 20, 20' and 22, 22' can each, if desired, be separated into smaller vessels arranged in series and references to "layers" of adsorbents above include arrangements in which the separate adsorbents are placed in separate vessels arranged in series.

EXAMPLES

Typically, these examples are run for 20 cycles to arrive at steady state conditions, in order to obtain the results below.

Example 1

Establishing Cycle Conditions

This example is an initial study conducted to determine whether conditions and apparatus suitable for conducting TPSA can be adapted for $N_2O$ removal. Cyclic, dynamic carbon dioxide and nitrous oxide breakthrough curves were measured on a two-layer bed. The first layer on the feed side is $K_2CO_3$ AA330 activated alumina (37% by volume) and the second layer on the product side is binderless Heng Ye Na exchanged LSX (63% by volume). The bed was fed water-saturated air at 20° C. (68° F.) and 6 bara (290 psia) and with a typical feed concentration of 400 ppmv $CO_2$ and 350 ppbv $N_2O$. The gas flux was 4,924 kg/m² hr. The data was obtained on a 203 mm (8 in) diameter by 2740 mm (9 ft) tall column. The analyser was placed 41% of the way along the length of the LSX zeolite. Under these conditions, no carbon dioxide was detected by the analyser during the online time. The conditions used, and the results in terms of removal of $CO_2$ and $N_2O$ were as follows:

TABLE 5

| | |
|---|---|
| Online time | 120 min |
| Purge/Air ratio (molar) | 0.25 |
| Hot purge temperature | 160° C. |
| Hot purge time | 30 min |
| Cold purge time | 70 min |
| Repressurisation/Depressurisation/parallel time | 20 min |
| Feed temperature | 19.3° C. |
| Feed pressure | 6.04 bara |
| Ratio of hot purge time to online time | 0.25 |
| Cycle type | Hybrid PSA/TSA |
| Number of adsorbent layers | 2 |
| $CO_2$ removal on alumina | 30-40% |
| $N_2O$ removal on molecular sieve | 93-94% |

Table 5 shows that a high removal of $N_2O$ is possible without using a CaX material. The degree of $N_2O$ removal obtained was comparable to that for a 180 min online time TSA process as taught in EP0992274.

Example 2

Variation of Cycle Conditions

Example 1 was repeated using a cycle time of 130 min and a hot purge time of 25 min (ratio of hot purge time to online time 0.19), and more than 95% of the $N_2O$ was removed.

In this invention, the process is not run to $CO_2$ breakthrough, and thus allows a greater proportion of the $CO_2$ to be adsorbed on the first adsorbent (40% compared with around 10% in a standard TSA process). This reduces the amount of $CO_2$ to be taken out by the molecular sieve and therefore improves the extent of removal of $N_2O$ on the molecular sieve.

Example 3

Effect of Zeolite Type 13X zeolite material was tested in the same conditions as Example 1, except that the feed temperature was reduced to 18.5° C., and the proportions of the adsorbent were 31.7% alumina and 68.3% 13X zeolite by volume. The $N_2O$ removal level obtained was 98%.

Little difference is seen between 13X and LSX zeolites in terms of $N_2O$ removal, although in U.S. Pat. No. 7,935,177 it is taught that Na exchanged LSX gives better performance for both $CO_2$ and $N_2O$ removal as shown in Table 6:

TABLE 6

| Zeolite | $CO_2$ relative dynamic adsorptivity | $N_2O$ relative Henry's Law constant for adsorption |
|---|---|---|
| 13X with 15% binder | 1.00 | 1.00 |
| NaLSX with 15% binder | 2.30 | 1.31 |

It was assumed that, given the high adsorption capacity of NaLSX for $CO_2$, only a small section of the NaLSX layer would have been used for $CO_2$ adsorption, especially as $CO_2$ removal with alumina as the first adsorbent is high. However, only a fraction of the NaLSX is located within the equilibrium zone in such short cycle conditions, meaning that the NaLSX is not used at its full capacity. This explains why a lower performing material such as 13X is showing similar results and therefore is a much more cost effective option. Also, the NaLSX is known to be more water sensitive, and to require a greater regeneration temperature in order to recover its full capacity.

Example 4

Improved Regeneration

Another way of improving the level of $N_2O$ removal is to increase the amount of energy added to the bed during regeneration. This is done at the expense of a higher heater power, but this also provides the possibility of extension of the cycle time.

Using the same equipment as described in Example 3, the results shown in Table 7 were obtained.

TABLE 7

| | Unit | Test 1 | Test 2 |
|---|---|---|---|
| Feed $CO_2$ Level | ppm | 400 | 400 |
| Online time | Min | 120 | 140 |
| Hot purge time | Min | 25 | 35 |
| Feed temperature | ° C. | 18.4 | 15 |
| Hot purge temperature | ° C. | 140 | 140 |
| Purge to air ratio (molar) | | 0.23 | 0.17 |
| $N_2O$ removal | % | 98 | 99 |
| Ratio of hot purge time to online time | % | 20 | 25 |
| Excess Heat | | 0.72 | 0.82 |

This shows that the cycle time can be extended by 20 min, provided that additional heating is added to the bed. The additional heat is measured in terms of excess heat, being the ratio of the heat supplied by the heater during regeneration to the heat of desorption of water, $CO_2$ and $N_2O$.

Example 5

Optimising Onstream Time

Figure 4:
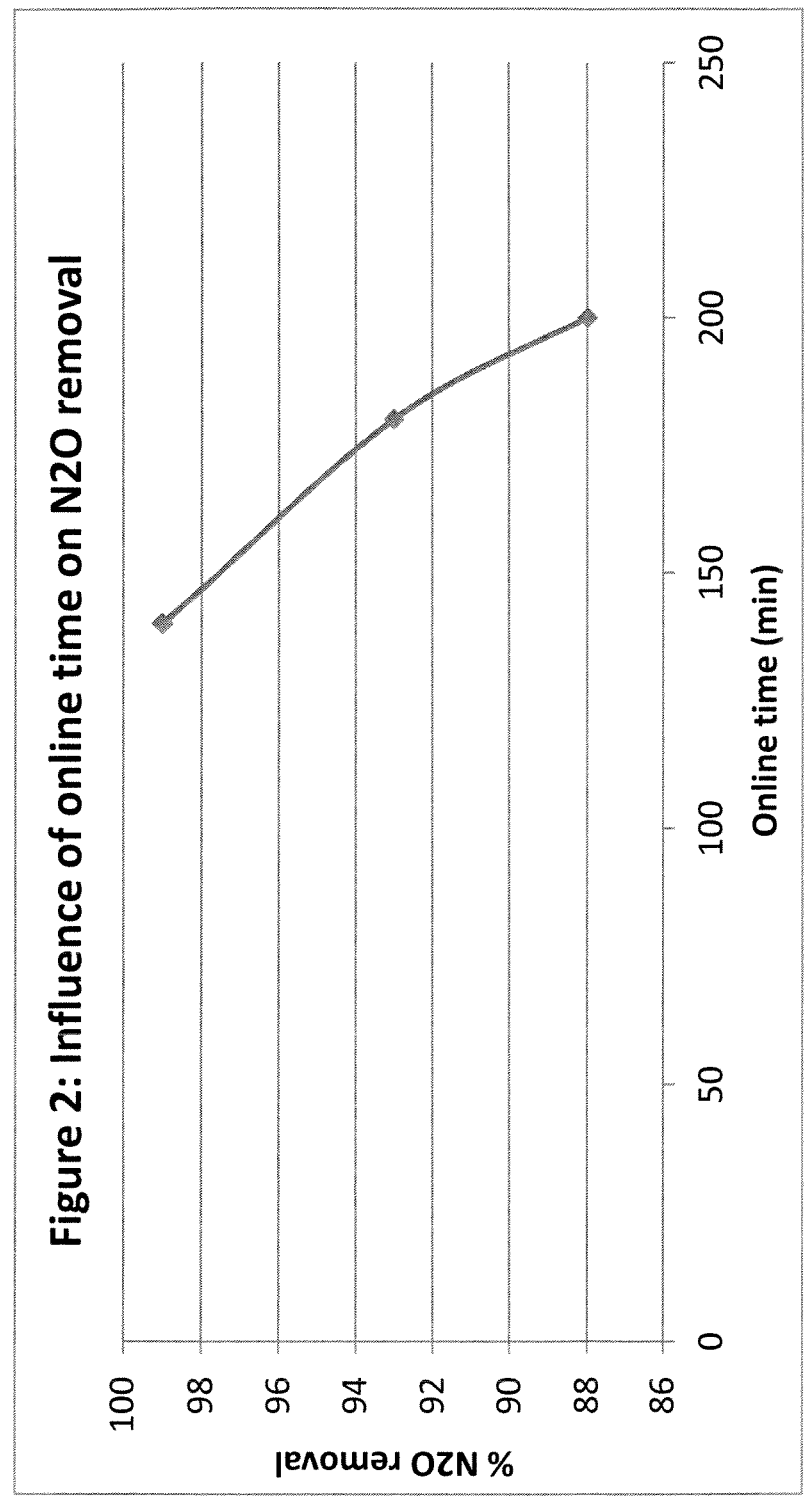
FIG. 4 shows the influence of online time on the level of $N_2O$ removal.

Under the conditions used above for Test 2, given in Table 7, the cycle time was extended to 180 min and then 200 min and the level of $N_2O$ removal was measured at 93% and 88% respectively. The results are shown in FIG. 4.

It is desirable to extend the cycle time in order to reduce the quantity of gas loss during the switching of beds from onstream to offstream and vice versa, especially in large plants in which the volume vented after each cycle is significant. In addition, in order to avoid excess heating of the product air stream, the heat pulse generated by adsorption must be either consumed or vented from the bed during regeneration. A short cycle time requires a higher regeneration gas flow rate in order to achieve that than a longer cycle time, and so it is preferred to extend the cycle time to reduce pressure drop penalties.

Example 6

Control Strategy

Figure 5:
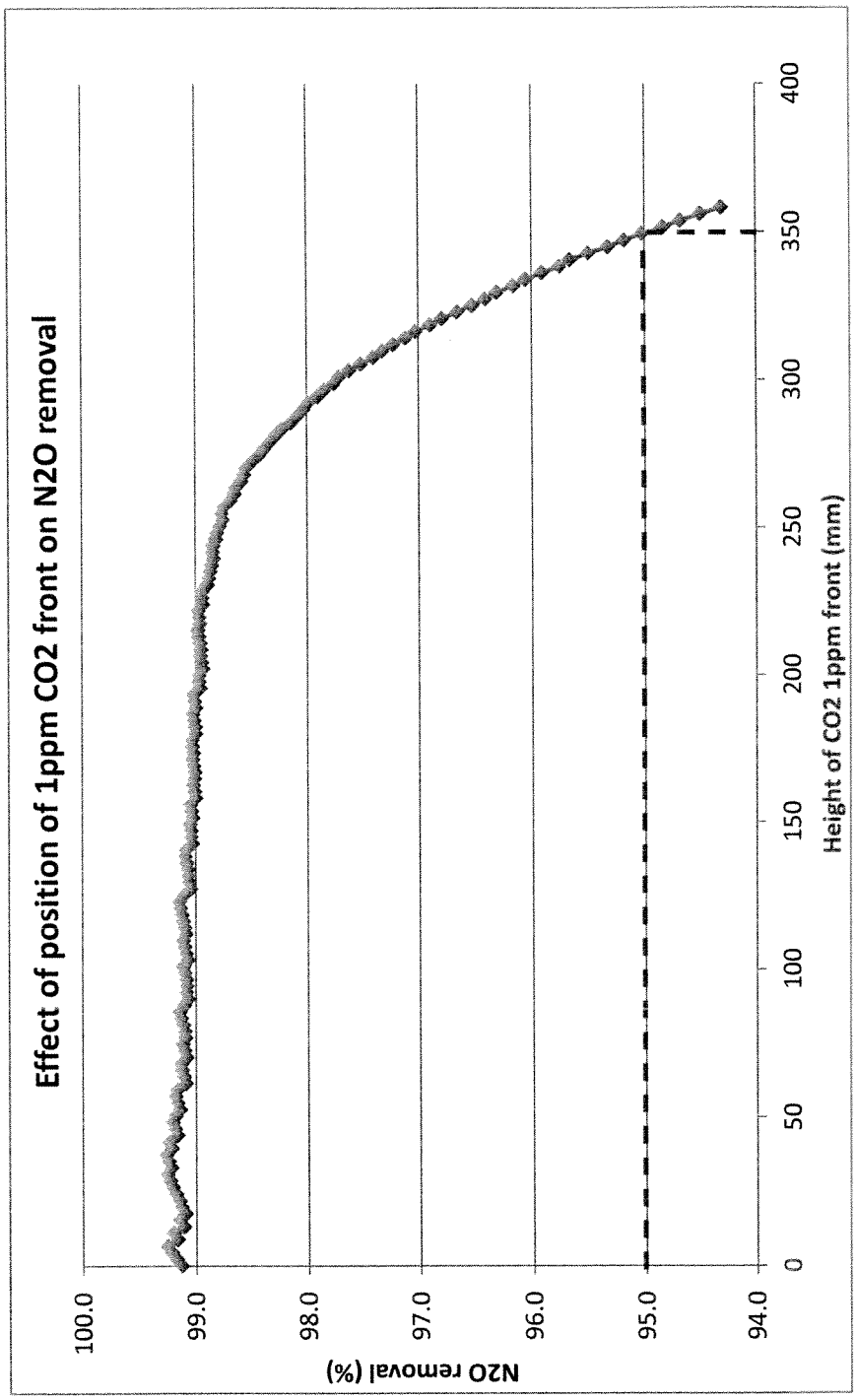
FIG. 5 shows the effect of the position in the adsorption bed of the 1 ppm $CO_2$ front on the level of $N_2O$ removal.

Under the conditions of Test 2, given in Table 7, the position of the $CO_2$ front (typically when an analyser would measure 1 ppmv of $CO_2$) is determined based on gas velocity in the bed. The second layer (molecular sieve) is composed of standard 13X material and occupies a column height of 820 mm. That position is then related to the amount of $N_2O$ removed, as shown in FIG. 5. Thus, if the analyser is positioned at the boundary between the first and second layers (zero on the horizontal axis of FIG. 5), at the time when the analyser detects 1 ppm $CO_2$, the removal of $N_2O$ at the end of the bed will be greater than 99%. If it is desired to obtain 99% $N_2O$ removal, this can be done by placing the analyser at any distance between 0 and 222 mm from the boundary between the first and second layers (up to 27% of the distance along the second layer); 98% removal can be obtained up to 290 mm from the boundary (up to 35% of the distance along the second layer); 97% removal up to 315 mm from the boundary (up to 38% of the distance along the second layer); 96% removal up to 335 mm from the boundary (up to 41% of the distance along the second layer); and 95% removal up to 349 mm from the boundary (up to 43% of the distance along the second layer). It is therefore possible to balance the cycle time with the degree of $N_2O$ removal as desired. Once the $CO_2$ is detected by the analyser, the bed is taken off line for regeneration. In comparison, a standard TSA is designed so that $CO_2$ is about to break through the end of the second layer at the end of the online time, making the $CO_2$ removal zone close to 100% of the total molecular sieve height, whereas, for 95% $N_2O$ removal, the $CO_2$ removal zone in the present invention is around 43% of the molecular sieve (second layer) height.

Examples 7 to 11

Removal of $CO_2$ and $N_2O$ from Air Feed Streams Containing a High Concentration of $CO_2$ Cyclic, dynamic carbon dioxide and nitrous oxide breakthrough curves were measured on a two-layer bed. The first layer on the feed side is 8% w/w $K_2CO_3$ co-formed Heng Ye activated alumina (31% by volume) and the second layer on the product side is Heng Ye HO 13X (69% by volume). The bed was fed water-saturated air at 7° C. and 5.64 bara and with a typical feed concentration of 325 ppbv $N_2O$. The gas flux was 5224 kg/m² h. The data was obtained on a 210 mm diameter by 1050 mm tall column. The conditions used were as follows:

TABLE 8

| Purge/Air ratio (molar) | 0.11 |
|---|---|
| Hot purge temperature | 150° C. |
| Feed temperature | 7° C. |
| Feed pressure | 5.64 bara |
| Cycle type | Hybrid PSA/TSA |
| Number of adsorbent layers | 2 |
| Analyser position along length of 13X bed | 41% |

The results obtained are shown in Table 9:

TABLE 9

| Example | On line time (min) | Cycle split (heat time/cool time/ switch time) | Average CO$_2$ in | % CO$_2$ removal by Alumina | % Total N$_2$O removal | % Total CO$_2$ Removal | Hot purge time/online time |
|---|---|---|---|---|---|---|---|
| 7 | 240 | 67/147/30 | 500 | 10% | 75% | 100% | 0.28 |
| 8 | 240 | 77/137/30 | 500 | 13% | 85% | 100% | 0.32 |
| 9 | 240 | 77/133/30 | 400 | 24% | 87% | 100% | 0.32 |
| 10 | 210 | 70/110/30 | 500 | 17% | 90% | 100% | 0.33 |
| 11 | 180 | 60/90/30 | 500 | 20% | 96% | 100% | 0.33 |

For Examples 7 to 10, the analyser measured a concentration of greater than 20 ppm CO$_2$ at the end of the online time, and as can be seen this corresponds with a N$_2$O removal level of 75-90%. In Example 11, the analyser measured a concentration of 20 ppm CO$_2$ at the end of the online time, corresponding to an N$_2$O removal level of 96%. Thus, the online time can be extended to as much as 240 min, with some decrease in the level of N$_2$O removal, which may in certain cases be acceptable.

Example 12

Removal of Hydrocarbon Impurities

The conditions set out in Examples 1 and 8 were compared with the conditions set out in U.S. Pat. No. 5,855,650 using alumina/13X or alumina/13X/CaX adsorbent configurations to determine their relative ability to remove a number of hydrocarbons from the feed air stream. All experiments were conducted with a water saturated feed air stream containing 400 ppm CO$_2$ and 320 ppb N$_2$O, except for the experiment under the conditions of Example 1 but using NaLSX, for which a 500 ppm CO$_2$ concentration was used.

TABLE 10

Comparison of TPSA cycles for impurities removal (expressed in % of feed concentration)

| Impurity | TPSA standard (13X) U.S. Pat. No. 5,855,650 | Short cycle TPSA (NaLSX) Current invention Example 1 | Short cycle TPSA (NaX) Current invention Example 8 | TPSA dual layers (CaX) U.S. Pat. No. 5,855,650 with 3 layers |
|---|---|---|---|---|
| Ethane | 15% | 15% | 11% | 15% |
| Ethylene | 60% | 95% | 97% | 100% |
| Acetylene | 100% | 100% | 100% | 100% |
| Propane | 35% | 80% | 67% | 45% |
| Propylene | 100% | 100% | 100% | 100% |
| Butene | 100% | 100% | 100% | 100% |
| N$_2$O | 30% | >85% | | >99% |

Comparative Example 1 - Conditions taught in U.S. Pat. No. 5,885,650

Two bed cyclic experiments for the removal of trace impurities from air were carried out in vessels 0.2 m in diameter. The length of the total adsorbent bed was 2 m. The feed air was saturated with water at feed conditions and contained 380 ppm CO$_2$ and 0.3 ppm N$_2$O. In all cases, the feed end of the adsorbent bed contained activated alumina (Alcan AA-300), and the product end of the bed contained 13X zeolite (Zeochem Z10-02, Si/Al=1.15). The experiments were carried out under the conditions shown in Table 11:

TABLE 11

| Feed time | 145 min |
|---|---|
| Heat time | 32 min at 165° C. |
| Cool time | 98 min at 35° C. |
| Switch time (depressurisation and repressurisation) | 15 min |
| Feed temperature | 35° C. |
| Feed pressure | 8.9 bara (890 kPa) |
| % N$_2$O removal at 20 ppb time average CO$_2$ breakthrough | 32.6% |
| Regeneration pressure | 1.05 bara (105 kPa) |
| P/A (molar basis) | 0.3 |
| Feed flow rate | 4.1 kmol/h |

The bed layering scheme was 75 vol % K$_2$CO$_3$ impregnated activated alumina (Alcan AA-320AP) on the feed end of the bed and 25 vol % 13X zeolite (Zeochem Z10-02) on the product end of the bed.

It can be seen that the present invention provides a significantly improved degree of N$_2$O removal compared with the conditions used in U.S. Pat. No. 5,885,650.

Whilst the invention has been described with reference to a preferred embodiment, it will be appreciated that various modifications are possible within the scope of the invention.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A method for determining conditions for the reduction, prior to cryogenic distillation, of the level of water, carbon dioxide and nitrous oxide in a feed air stream in a process comprising:
   (a) passing said feed air stream at a feed pressure in a feed direction through a first adsorbent which has a Henry's Law selectivity for carbon dioxide over nitrous oxide measured at 30° C. of at least 12.5, and subsequently through a second adsorbent whose Henry's Law constant for the adsorption of N$_2$O measured at 30° C. is less than 500 mmol/g/atm and whose Henry's Law selectivity for CO$_2$ over N$_2$O is at most 5;
   (b) ceasing to pass said feed air stream to said first and second adsorbents after a first time period;

(c) depressurising the gas in contact with the first and second adsorbents to a second pressure less than the feed pressure;
(d) passing regenerating gas at the second pressure and at a first temperature which is in the range 140 to 220° C. to at least the second adsorbent in a direction opposite to the feed direction for a second time period, and subsequently passing the regenerating gas at the second pressure and a second temperature less than the first temperature to the second and first adsorbents in a direction opposite to the feed direction for a third time period;
(e) ceasing passing regenerating gas to the first and second adsorbents;
(f) repressurising the gas in contact with the first and second adsorbents to the feed pressure;
(g) repeating steps (a) to (f);
wherein the first adsorbent occupies from 25% to 40% by volume of the total volume occupied by the first and second adsorbents; and wherein the molar ratio of the regenerating gas to the feed air supplied during each iteration of the steps (a) to (f) is from 0.08 to 0.5;
which method comprises:
(i) placing an analyser for $CO_2$ concentration measurement at a chosen position within the length of the second adsorbent;
(ii) determining the threshold concentration measured by the $CO_2$ analyser when a desired maximum level of $N_2O$ is simultaneously obtained at the downstream end of the second adsorbent in the feed direction;
(iii) using the result of step (ii) to determine the maximum duration of the first time period, such that the maximum duration of the first time period is the time taken from commencing passing the feed air stream to the first and second adsorbents to the measurement by the analyser of the determined threshold concentration of $CO_2$.

2. The method of claim 1, wherein the analyser for measurement of the concentration of $CO_2$ is placed at a point is up to 45% of the way along the length of the second adsorbent in the feed direction.

3. The method of claim 1, wherein the nitrous oxide level downstream of the second adsorbent is at most 20% of its original level in the feed air stream.

4. A process for the reduction of the level of water, carbon dioxide and nitrous oxide in a feed air stream prior to cryogenic distillation, comprising:
(a) passing said feed air stream at a feed pressure in a feed direction through a first adsorbent which has a Henry's Law selectivity for carbon dioxide over nitrous oxide measured at 30° C. of at least 12.5, and subsequently through a second adsorbent whose Henry's Law constant for the adsorption of $N_2O$ measured at 30° C. is less than 500 mmol/g/atm and whose Henry's Law selectivity for $CO_2$ over $N_2O$ is at most 5;
(b) ceasing to pass said feed air stream to said first and second adsorbents after a first time period;
(c) depressurising the gas in contact with the first and second adsorbents to a second pressure less than the feed pressure;
(d) passing regenerating gas at the second pressure and at a first temperature which is in the range 140 to 220° C. to at least the second adsorbent in a direction opposite to the feed direction for a second time period, and subsequently passing the regenerating gas at the second pressure and a second temperature less than the first temperature to the second and first adsorbents in a direction opposite to the feed direction for a third time period;
(e) ceasing passing regenerating gas to the first and second adsorbents;
(f) repressurising the gas in contact with the first and second adsorbents to the feed pressure;
(g) repeating steps (a) to (f);
wherein the first adsorbent occupies from 25% to 40% by volume of the total volume occupied by the first and second adsorbents;
wherein the method further comprises:
(i) placing an analyser for $CO_2$ concentration measurement at a chosen position within the length of the second adsorbent; and
(ii) determining the threshold concentration measured by the $CO_2$ analyser when a desired maximum level of $N_2O$ is simultaneously obtained at the downstream end of the second adsorbent in the feed direction;
wherein the maximum duration of the first time period is the time taken from commencing passing the feed air stream to the first and second adsorbents to the measurement by the analyser of the determined threshold concentration of $CO_2$; and
wherein the molar ratio of the regenerating gas to the feed air supplied during one iteration of the steps (a) to (f) is from 0.08 to 0.5.

5. The process of claim 4, wherein the second adsorbent is selected from the group consisting of NaX having a Si/Al ratio of from 1.25 to 1.0, 4A zeolite, 5A zeolite, mordenite, chabazite and clinoptilolite.

6. The process of claim 4, wherein the analyser for measurement of the concentration of $CO_2$ is placed at a point is up to 45% of the way along the length of the second adsorbent in the feed direction.

7. The process of claim 4, wherein the ratio of the second time period to the first time period is less than 35%.

8. The process of claim 4, wherein the first time period is from 100 to 300 min.

9. The process of claim 4, wherein the second time period is from 20 min to 100 min.

10. The process of claim 4, wherein the temperature of the heated regenerating gas is from 140 to 180° C.

11. The process of claim 4, wherein the third time period is from 50 to 220 min.

12. The process of claim 4, wherein the first adsorbent occupies from 28% to 37% by volume of the total volume occupied by the first and second adsorbents.

13. The process of claim 5, wherein the second adsorbent is selected from NaX zeolite having a Si/Al ratio of from 1.25 to 1.0 and 5A zeolite.

14. The process of claim 4, wherein the first adsorbent is selected from alumina or impregnated alumina.

15. The process of claim 4, wherein the nitrous oxide level downstream of the second adsorbent is at most 20% of its original level in the feed air stream.

16. An apparatus for the reduction of the level of water, carbon dioxide and nitrous oxide from a feed air stream prior to cryogenic distillation, comprising:
in an adsorbent bed, a layer of a first adsorbent which has a Henry's Law selectivity for carbon dioxide over nitrous oxide measured at 30° C. of at least 12.5 and a second adsorbent whose Henry's Law constant for the adsorption of $N_2O$ measured at 30° C. is less than 500 mmol/g/atm and whose Henry's Law selectivity for $CO_2$ over $N_2O$ is at most 5, wherein the first adsorbent occupies from 25% to 40% by volume of the total volume occupied by the first and second adsorbents; and
an analyser for carbon dioxide placed within the length of the second adsorbent.

17. The apparatus of claim 16, wherein the analyser for measurement of the concentration of $CO_2$ is placed at a point is up to 45% of the way along the length of the second adsorbent in the feed direction.

18. The apparatus of claim 16, wherein the second adsorbent is selected from the group consisting of NaX having a Si/Al ratio of from 1.25 to 1.0, 4A zeolite, 5A zeolite, mordenite, chabazite and clinoptilolite.

19. The apparatus of claim 18, wherein the second adsorbent is selected from NaX zeolite having a Si/Al ratio of from 1.25 to 1.0 and 5A zeolite.

20. The apparatus of claim 16, wherein the first adsorbent is selected from alumina or impregnated alumina.

21. The apparatus of claim 16, wherein the first adsorbent occupies from 28% to 37% by volume of the total volume occupied by the first and second adsorbents.

22. A method of upgrading an apparatus designed to reduce the levels of carbon dioxide, nitrous oxide and water from a feed air stream by a temperature swing adsorption process in order that it can provide a reduction in the level of nitrous oxide in the feed air stream without use of an adsorbent having a Henry's Law selectivity measured at 30° C. for nitrous oxide compared to carbon dioxide of 0.5 or more, in which the adsorbents contained in the apparatus are removed and replaced with an identical total volume of adsorbent consisting of a layer of a first adsorbent which has a Henry's Law selectivity for carbon dioxide over nitrous oxide measured at 30° C. of at least 12.5 and a second adsorbent whose Henry's Law constant for the adsorption of $N_2O$ measured at 30° C. is less than 500 mmol/g/atm and whose Henry's Law selectivity for $CO_2$ over $N_2O$ is at most 5, wherein the first adsorbent occupies from 25% to 40% by volume of the total volume occupied by the first and second adsorbents, and in which an analyser for carbon dioxide is placed within the length of the second adsorbent.

23. The method of claim 22, wherein the analyser for measurement of the concentration of $CO_2$ is placed at a point is up to 45% of the way along the length of the second adsorbent in the feed direction.

24. The method of claim 22, wherein the second adsorbent is selected from the group consisting of NaX having a Si/Al ratio of from 1.25 to 1.0, 4A zeolite, 5A zeolite, mordenite, chabazite and clinoptilolite.

25. The method of claim 24, wherein the second adsorbent is selected from NaX zeolite having a Si/Al ratio of from 1.25 to 1.0 and 5A zeolite.

26. The method of claim 22, wherein the first adsorbent is selected from alumina or impregnated alumina.

27. The method of claim 22, wherein the first adsorbent occupies from 28% to 37% by volume of the total volume occupied by the first and second adsorbents.

* * * * *